United States Patent
Ball et al.

(10) Patent No.: US 10,107,825 B2
(45) Date of Patent: Oct. 23, 2018

(54) SYSTEM AND METHOD INCORPORATING SOLID BUFFER

(71) Applicant: LIFE TECHNOLOGIES CORPORATION, Carlsbad, CA (US)

(72) Inventors: James A. Ball, Ledyard, CT (US); Jonathan Schultz, Guilford, CT (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 364 days.

(21) Appl. No.: 14/741,084

(22) Filed: Jun. 16, 2015

(65) Prior Publication Data

US 2015/0369828 A1    Dec. 24, 2015

Related U.S. Application Data

(60) Provisional application No. 62/036,303, filed on Aug. 12, 2014, provisional application No. 62/014,636, filed on Jun. 19, 2014.

(51) Int. Cl.
    *C12Q 1/68*     (2018.01)
    *G01N 33/84*    (2006.01)
    *C12Q 1/6869*   (2018.01)
    *B01J 19/00*    (2006.01)

(52) U.S. Cl.
    CPC .......... *G01N 33/84* (2013.01); *B01J 19/0086* (2013.01); *C12Q 1/6869* (2013.01)

(58) Field of Classification Search
    None
    See application file for complete search history.

(56) References Cited

U.S. PATENT DOCUMENTS

| | | | |
|---|---|---|---|
| 2002/0115957 A1* | 8/2002 | Sun ................... | A61M 37/0015 604/20 |
| 2011/0217697 A1* | 9/2011 | Rothberg ............. | C12Q 1/6874 435/6.1 |
| 2015/0024414 A1* | 1/2015 | Harper ............. | G01N 33/56911 435/7.35 |

FOREIGN PATENT DOCUMENTS

| | | |
|---|---|---|
| WO | 00/12173 | 3/2000 |
| WO | 2010/008480 | 1/2010 |
| WO | 2012/054104 | 4/2012 |
| WO | WO-2015/195690 | 12/2015 |

OTHER PUBLICATIONS

PCT/US2015/036068, International Preliminary Report on Patentability, dated Dec. 29, 2016, 1-11.
International Search Report and Written Opinion of the International Searching Authority for International Application No. PCT/US2015/036068 dated Dec. 4, 2015, 17 pages.

* cited by examiner

*Primary Examiner* — David C Thomas

(57) ABSTRACT

A buffered suspension includes a surfactant and a solid buffer particulate having a point of zero charge at least 1.2 pH units different that the pH of the buffered suspension. The buffered suspension can be prepared by mixing a stock solution with the solid buffer particulate and titrating. A method of preforming a pH sensitive process includes drawing the buffered suspension from a reservoir, filtering the solid buffer particulate from the buffered suspension, and applying the filtered solution to a sensor.

20 Claims, 3 Drawing Sheets

SYSTEM AND METHOD INCORPORATING SOLID BUFFER

CROSS-REFERENCE TO RELATED APPLICATION(S)

This application claims benefit of U.S. Provisional Application No. 62/014,636, filed Jun. 19, 2014, which is incorporated herein by reference in its entirety.

This application claims benefit of U.S. Provisional Application No. 62/036,303, filed Aug. 12, 2014, which is incorporated herein by reference in its entirety.

FIELD OF THE DISCLOSURE

This disclosure, in general, relates to systems and methods incorporating a solid buffer in reagent solutions.

BACKGROUND

As research and medical testing seeks to characterize small concentrations of complex molecules, the sensitivity of instruments is increasingly susceptible to changes in pH. Further, such advanced sensing and testing methods rely on expensive reagents that are difficult to prepare. In a particular example, sequencing of nucleic acids or proteins relies on specialized solutions, such as nucleotide solutions that include expensive components. Such testing methods utilizing such specialized solutions can be pH sensitive.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1:
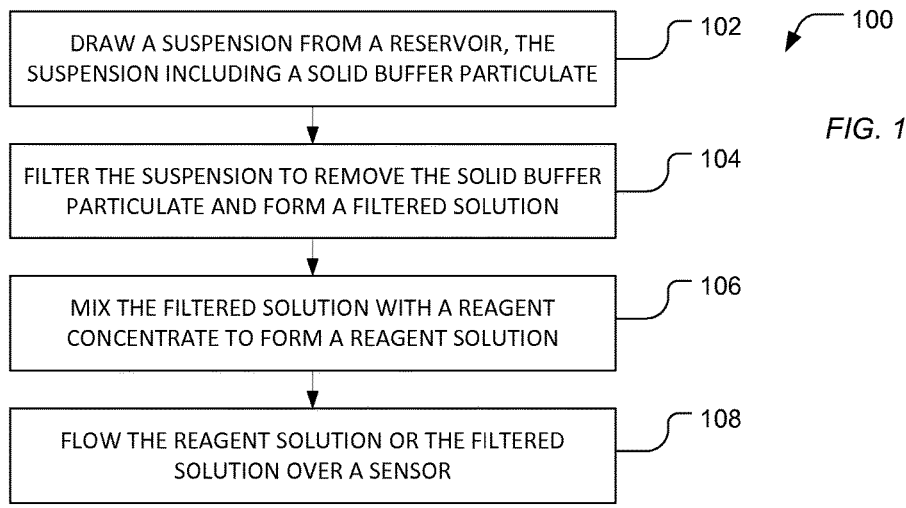
FIG. 1 includes a flow diagram illustrating an exemplary method for utilizing a buffered suspension.

In an exemplary embodiment, a buffered suspension includes a surfactant and a solid buffer particulate. The buffered suspension has a target pH. The solid buffer particulate may be a ceramic buffer particulate that has, for example, a point of zero charge that is at least 1.2 pH units different than the target pH of the suspension. In use, the suspension can be drawn from a reservoir and the solid buffer particulate filtered from the suspension. The filtered solution can be applied over a sensor or can be used to form other reagent solutions from reagent concentrates. In an example, the buffered suspension can be formulated by mixing a stock solution including the surfactant and optionally other components with the solid buffer particulate to form a suspension. The suspension can be titrated either with an acid or base to a target pH. The solid buffer particulate can be allowed to settle and a portion of the stock solution can be decanted. Additional stock solution can be added and the process repeated. Subsequently, the suspension can be placed in bottles for transportation or cartridges for insertion into the sensor system.

In particular, the buffered suspension can include a surfactant and a solid buffer particulate. The buffer suspension has pH within a target range. For example, the target pH can be within a range of 6.0 to 8.0, such as a range of 6.8 to 8.0, a range of 7.2 to 8.0, or even a range of 7.4 to 8.0. Alternatively, the target pH can be in a range of 5.0 to 6.0. In a further alternative, the target pH can be in a range of 9.0 to 11.0.

The solid buffer particulate can include a ceramic particulate. In an example, the ceramic particulate can be titanium dioxide, tin oxide, zirconia, alumina, tantalum oxide, or a combination thereof. For example, the ceramic particulate can be a titanium dioxide or tin oxide. In a particular example, the ceramic particulate includes titanium dioxide. Further, the ceramic particulate can be a hydrolyzed ceramic particulate or can be a fumed ceramic particulate. In particular, the ceramic particulate is a fumed ceramic particulate.

The solid buffer particulate, such as a ceramic particulate, can have a point of zero charge at least 1.2 pH units different than the target pH. For example, the point of zero charge can be at least 2.0 pH units different than a target pH or at least 3.0 pH units different than the target pH, but not greater than 10 pH units different than the target pH. In particular, the solid buffer particulate has a point of zero charge that is less than the target pH of the suspension. Alternatively, the solid buffer particulate can have a point of zero charge that is greater than the target pH of the suspension. In a further alternative, a combination of solid buffer particulates can be used. For example, a combination including a solid buffer particulate having a point of zero charge below the target pH and a solid buffer particulate having a point of zero charge above the target pH can be used.

Further, the solid buffer particulate can have a specific surface area in the range of 10 $m^2/g$ to 350 $m^2/g$. For example, the specific surface area can be in a range of 50 $m^2/g$ to 350 $m^2/g$, such as a range of 100 $m^2/g$ to 300 $m^2/g$, a range of 150 $m^2/g$ to 300 $m^2/g$, or even a range of 225 $m^2/g$ to 275 $m^2/g$. In another example, the specific surface area can be in a range of 25 $m^2/g$ to 125 $m^2/g$, such as a range of 50 $m^2/g$ to 100 $m^2/g$. Further, the solid buffer particulate can have a particle size, such as an average agglomerate size, in a range of 0.01 μm to 1200 μm. For example, the average particle size can be in a range of 0.05 μm to 500 μm, such as a range of 0.5 μm to 200 μm, or even a range of 5.0 μm to 100 μm.

The suspension can include the solid buffer particulate in a range of 1 g/L to 100 g/L, such as a range of 5 g/L to 75 g/L, a range of 10 g/L to 65 g/L, a range of 20 g/L to 50 g/L, or even a range of 25 g/L to 40 g/L.

The suspension can include one or more surfactants having a total concentration in the range of 0.001% to 1.0% by weight. For example, the surfactant can be included in an amount in a range of 0.005% to 0.8%, such as a range of 0.005% to 0.5% by weight.

The surfactant can be an ionic surfactant, an amphoteric surfactant, a non-ionic surfactant, or a combination thereof. Optionally, the surfactant can include a zwitterion. The ionic surfactant can be an anionic surfactant. An exemplary anionic surfactant includes a sulfate surfactant, a sulfonate surfactant, a phosphate surfactant, a carboxylate surfactant, or any combination thereof. An exemplary sulfate surfactant includes alkyl sulfates, such as ammonium lauryl sulfate, sodium lauryl sulfate (sodium dodecyl sulfate, (SDS)), or a combination thereof; an alkyl ether sulfate, such as sodium laureth sulfate, sodium myreth sulfate, or any combination thereof; or any combination thereof. An exemplary sulfonate surfactant includes an alkyl sulfonate, such as sodium dodecyl sulfonate; docusates such as dioctyl sodium sulfosuccinate; alkyl benzyl sulfonate (e.g., dodecyl benzene sulfonic acid or salts thereof); or any combination thereof. An exemplary phosphate surfactant includes alkyl aryl ether phosphate, alkyl ether phosphate, or any combination thereof. An exemplary carboxylic acid surfactant includes alkyl carboxylates, such as fatty acid salts or sodium stearate; sodium lauroyl sarcosinate; a bile acid salt, such as sodium deoxycholate; or any combination thereof.

In another example, the ionic surfactant can be a cationic surfactant. An exemplary cationic surfactant includes primary, secondary or tertiary amines, quaternary ammonium surfactants, or any combination thereof. An exemplary quaternary ammonium surfactant includes alkyltrimethylammonium salts, such as cetyl trimethylammonium bromide (CTAB) or cetyl trimethylammonium chloride (CTAC); cetylpyridinium chloride (CPC); polyethoxylated tallow amine (POEA); benzalkonium chloride (BAC); benzethonium chloride (BZT); 5-bromo-5-nitro-1,3-dioxane; dimethyldioctadecylammonium chloride; dioctadecyldimethylammonium bromide (DODAB); or any combination thereof.

An exemplary amphoteric surfactant includes a primary, secondary, or tertiary amine or a quaternary ammonium cation and a sulfonate, carboxylate, or phosphate anion. An exemplary sulfonate amphoteric surfactant includes (3-[(3-cholamidopropyl)dimethylammonio]-1-propanesulfonate); a sultaine such as cocamidopropyl hydroxysultaine; or any combination thereof. An exemplary carboxylic acid amphoteric surfactant includes amino acids, imino acids, betaines such as cocamidopropyl betaine, or any combination thereof. An exemplary phosphate amphoteric surfactant includes lecithin. In a further example, the surfactant can be a sulfobetaine surfactant or an amidosulfobetaine.

In another example, the surfactant can be a non-ionic surfactant such as a polyethylene glycol-based surfactant, an alkyl pyrrolidine surfactant, an alkyl imidazolidinone surfactant, an alkyl morpholine surfactant, an alkyl imidazole surfactant, an alkyl imidazoline surfactant, or a combination thereof. In a particular example, the polyethylene-glycol-based surfactant includes a polyethylene-glycol ether, such as an alkylphenol polyethoxylate, such as octyl phenol ethoxylate or a polyoxyethylene alkyl phenyl ether, or a combination thereof. In another example, the non-ionic surfactant includes a non-ionic fluorosurfactant, such as an ethoxylated fluorocarbon. In a further example, the suspension can include octyl pyrrolidine.

Further, the suspension can include a biocide. In a particular example, the biocide can be an isothiazolinone biocide. For example, the biocide can be 2-methyl4-isothiazoline-3-one.

The suspension can include salts, such as magnesium salt, potassium salt, sodium salt, or a combination thereof. For example, the suspension can include potassium salt, such as potassium chloride, in a range of 5 mM to 150 mM, such as a range of 10 mM to 100 mM or a range of 40 mM to 70 mM. In another example, the suspension can include a magnesium salt, such as magnesium chloride or magnesium sulfate, in a range of 1 mM to 100 mM, such as a range of 5 mM to 75 mM or a range of 5 mM to 30 mM. In a further example, the suspension can include sodium salt, such as sodium chloride, in a range of 5 mM to 150 mM, such as a range of 10 mM to 100 mM or a range of 40 mM to 70 mM.

As illustrated in FIG. 1, a method 100 includes drawing a suspension from a reservoir, as illustrated at 102. The suspension includes a solid buffer particulate and can include a surfactant. The suspension is filtered, as illustrated at 104, to remove the solid buffer particulate and form a filtered solution. The filter solution can be used to mix with a reagent concentrate to form a reagent solution, as illustrated at 106. The reagent solution or the filtered solution can flow over a sensor, as illustrated at 108, as part of a process for testing, measuring or sensing. In a particular example, alternate flows of the filtered solution and reagent solutions can flow over the sensor. As such, the filtered solution can act as a wash solution between flows of the reagent solutions. The sensor can be a pH sensor. In a particular example, the sensor may be a biosensor, such as a semiconductor sequencing device. An exemplary semiconductor sequencing device can rely on pH to perform sequencing-by-synthesis.

Figure 2:
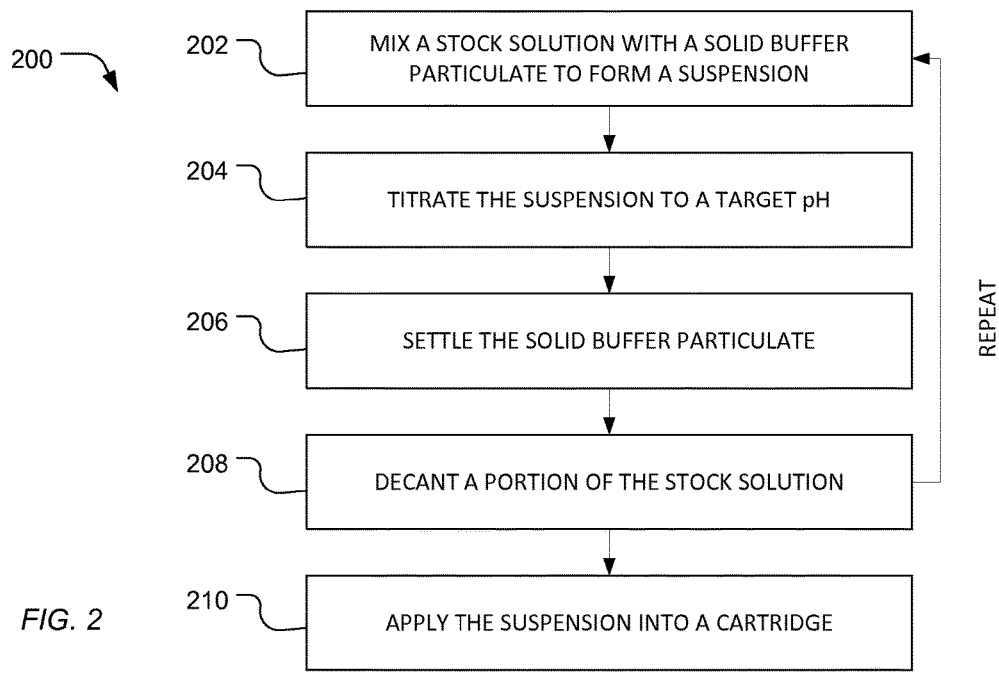
FIG. 2 includes a flow diagram illustrating an exemplary method for formulating a buffered suspension.

The suspension can include a stock solution and a solid buffer particulate. As illustrated in FIG. 2, a method 200 includes mixing a stock solution with a solid buffer particulate to form a suspension, as illustrated at 202. The stock solution can include the components of the final buffered suspension, for example, as described above, absent the solid buffer particulate. The dispersion is titrated to a target pH, as illustrated at 204. For example, the pH can be adjusted using a base or an acid. For example, the pH can be adjusted using a base, such as sodium hydroxide, or an acid, such as hydrochloric acid.

As illustrated at 206, the solid buffer particulate can settle and a portion of the stock solution can be decanted, as illustrated at 208. The process can be repeated, mixing additional stock solution with the solid buffer particulate, as illustrated at 202, titrating, as illustrated at 204, allowing the buffer particulate to settle, as illustrated at 206, and decanting a portion of the stock solution, as illustrated at 208. The process can be repeated once, twice, three times, or more. Subsequently, the solid buffer particulate can be re-dispersed within the suspension and applied to a cartridge useful in a system for sensing or testing, as illustrated at 210.

Figure 3:
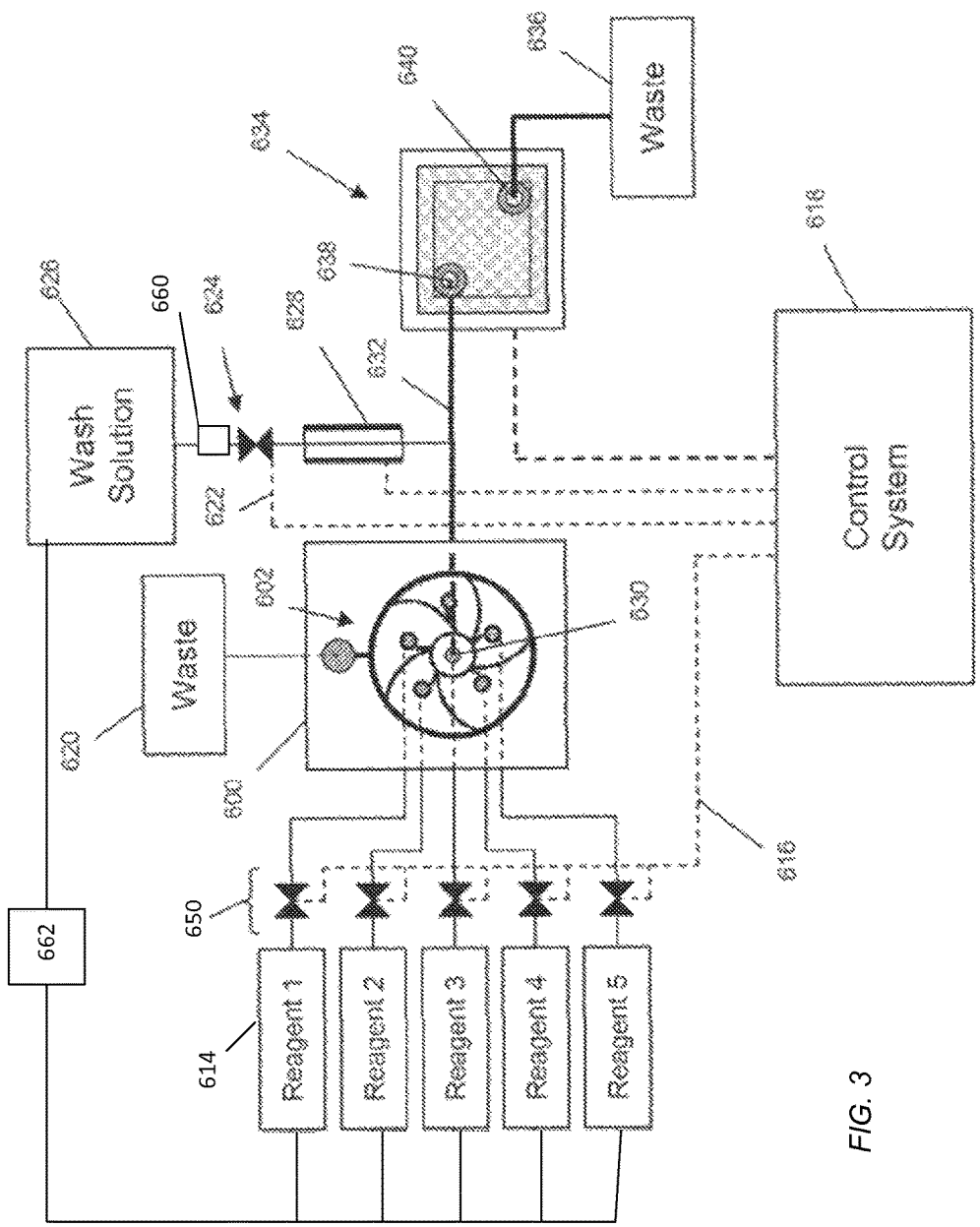
FIG. 3 includes an illustration of an exemplary testing apparatus using a buffered suspension.

FIG. 3 includes an illustration of an exemplary system in which such a buffered suspension finds particular use. The exemplary buffered suspension finds particular use in biological processes where multiple reagents are delivered to one or more reactors or reaction sites. The reaction sites may be monitored by chemical, electrical or optical sensors. Exemplary systems include methods and apparatuses for carrying out DNA sequencing, and in particular, pH-based DNA sequencing. For example, in pH-based DNA sequencing, nucleotide base incorporations are determined by measuring hydrogen ions that are generated as natural byproducts of polymerase-catalyzed extension reactions. DNA templates each having a primer and polymerase operably bound are loaded into reaction chambers or microwells, after which repeated cycles of deoxynucleoside triphosphate (dNTP) addition and washing are carried out. Such templates are typically attached as clonal populations to a solid support, such as a microparticle, bead, or the like, and such clonal populations are loaded into reaction chambers. In each addition step of the cycle, the polymerase extends the primer by incorporating added dNTP when the next base in the template is the complement of the added dNTP. If there is one complementary base, there is one incorporation, if two, there are two incorporations, if three, there are three incorporations, and so on. With each such incorporation there is a hydrogen ion released, and collectively a population of templates releasing hydrogen ions causes very slight changes to the local pH of the reaction chamber which is detected by an electronic sensor. In addition to sequencing, the device herein may be useful for other biological instruments that require fluid storage or delivery.

FIG. 3 diagrammatically illustrates a system employing an enclosure 614 that is a reagent reservoir, for example, for carrying out pH-based nucleic acid sequencing. Each electronic sensor of the apparatus generates an output signal. The fluid circuit permits multiple reagents to be delivered to the reaction chambers.

In FIG. 3, the system includes a fluidics circuit 602 connected to the reagent reservoirs 614, to a waste reservoir 620, and to a biosensor 634 by fluid pathway 632 that connects fluidics node 630 to inlet 638 of biosensor 634 for fluidic communication. The prepared and mixed reagent solution from reservoirs 614 can be driven to fluidic circuit 602 by a variety of methods including pressure, pumps, such as syringe pumps, gravity feed, and the like, and are selected by control of valves 650. Reagents from the fluidics circuit 602 can be driven to the waste containers 620 and 636. The control system 618 includes controllers for valves 650 that generate signals for opening and closing via an electrical connection 616.

The control system 618 also includes controllers for other components of the system, such as a wash solution valve 624 connected thereto by the electrical connection 622, and the reference electrode 628. The control system 618 can also include control and data acquisition functions for the biosensor 634. In one mode of operation, the fluidic circuit 602 delivers a sequence of selected reagents 1, 2, 3, 4, or 5 to the biosensor 634 under programmed control of the control system 618, such that in between selected reagent flows, the fluidics circuit 602 is primed and washed with a wash solution 626, and the biosensor 634 is washed with the wash solution 626. Fluids entering the biosensor 634 exit through the outlet 640 and are deposited in the waste container 636. A similar setup may be used for optical sequencing systems, with photodiodes or CCD cameras, for example.

In a particular example, the wash solution 626 can be a buffered suspension including the solid buffer particulate. The buffer suspension (wash solution) can be filtered using a filter 660 before entering the fluidics circuit 602 or sensor 634. In a further example, the buffered suspension can be applied to the reagent reservoirs 614 through filter 662 to form the reagent solutions from reagent concentrate within the reagent reservoirs. Alternatively, the filter 660 and 662 can be the same filter. In an example, the reagent concentrate is a liquid concentrate. In another example, the reagent concentrate is a dried concentrate, such as a lyophilized reagent (e.g., lyophilized nucleotides). Alternatively, the illustrated filters 660 and 662 can be combined. In another example, filters can be located downstream of the reagent reservoirs 614, such as between the reagent reservoirs 614 and the valves 650.

Aspects of the above methods, systems, and compositions provide technical advantages, including a buffered suspension that counteracts acidification by outside influences, such as a carbon dioxide. The suspension can be filtered to remove buffering, allowing for use in systems that measure changes in pH. In particular, for systems using pH sensors, providing buffering during reagent transport or storage yet allowing for pH changes during use is problematic. Utilizing a filterable solid state buffer, allows robust pH control during transportation and storage, while presenting a solution useful in systems that utilize pH changes.

EXAMPLE

Example 1

A suspension is prepared by the following procedure. Nitrogen purge clean 2 liter bottles for 5 minutes, add 1880 ml 18 mOhm water, add 120 ml wash solution, mix briefly under nitrogen.

The wash solution is prepared by the following process. Firstly, weigh 200 g titanium oxide into clean 8 L carboy outfitted with spigot, add 8 L PSP4 W2, keep carboy under nitrogen and mix with rotary mixer on stand in chemistry area, add 20 ml M NaOH, mix for 30 minutes, check pH using special glass pH probe with sliding sheath, keep probe suspended in slurry, titrate to pH 7.85 using 1M NaOH, adding 1 ml at a time, mix for 10 minutes, stop mixing, allow slurry to settle for 30 minutes, and slowly decant top 4 L of liquid, limiting disturbance of titania.

Secondly, add freshly made 4 L PSP4 W2, mix 10 minutes, check pH and record, stop mixing, allow slurry to settle for 30 minutes, and slowly decant top 4 L of liquid, limiting disturbance of titania, allow slurry to settle for 30 minutes, and slowly decant top 4 L of liquid, limiting disturbance of titania.

Thirdly, add freshly made 4 L PSP4 W2, mix 10 minutes, check pH and record, stop mixing, allow slurry to settle for 30 minutes, slowly decant down to 6 L volume of slurry, start mixing again, and bring pH to 7.85 using 1M NaOH, adding ~500 ul at a time.

Example 2

Figure 4:
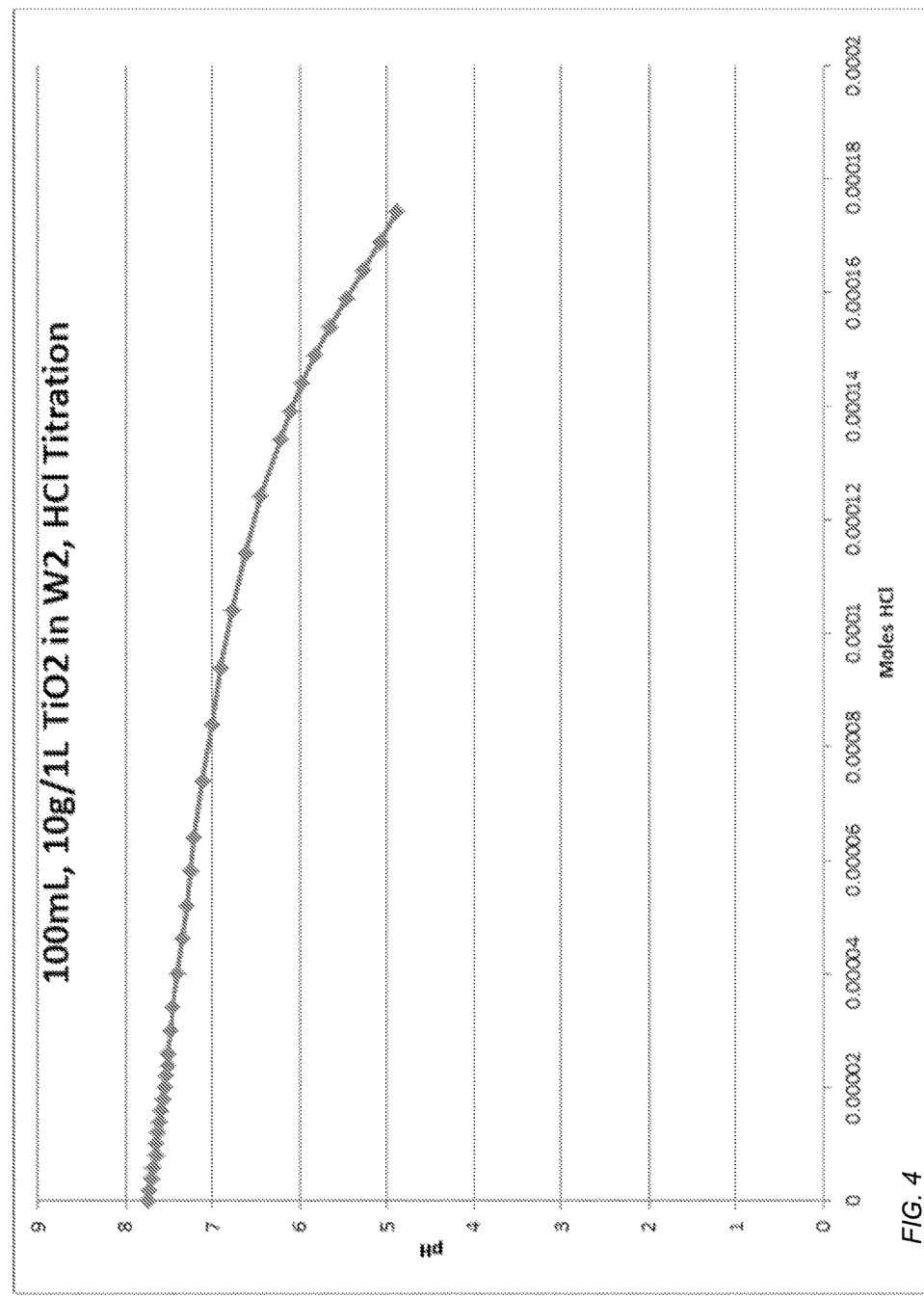
FIG. 4 includes a graph illustrating the response of a buffered suspension to a strong acid.

The pH response of a 100 mL sample including titania in a W2 solution at a concentration of 10 g/L is tested. An HCl solution is mixed with the sample and the pH response is measured. As illustrated in FIG. 4, the pH of the sample exhibits resistance to pH change in response to the addition of the HCl.

In a first aspect, a method of performing pH-sensitive processes includes drawing a suspension from a reservoir, the suspension including a surfactant and a solid buffer particulate and having a target pH; filtering the solid buffer particulate from the suspension to form a filtered solution; and flowing the filtered solution over a sensor.

In a second aspect, a method of forming a suspension includes mixing a stock solution and a solid buffer particulate to form a suspension, the stock solution comprising a surfactant; titrating the suspension to a target pH; settling the solid buffer particulate from the suspension; and decanting a portion of the stock solution.

In a third aspect, a buffered suspension includes a surfactant and a solid buffer particulate having a point of zero charge at least 1.2 pH units different that the pH of the buffered suspension.

In an example of the first, second, and third aspects, the solid buffer particulate has a point of zero charge of at least 1.2 pH units different than the target pH. For example, the point of zero charge is at least 2.0 pH units different than the target pH, such as at least 3.0 pH units different than the target pH, but not greater than 10 pH units different than the target pH.

In another example of the first, second, and third aspects and the above examples, the target pH is in a range of 6 to 8. For example, the target pH is in a range of 6.8 to 8.0, such as a range of 7.2 to 8.0 or a range of 7.4 to 8.0.

In a further example of the first, second, and third aspects and the above examples, the solid buffer particulate includes a ceramic particulate. For example, the ceramic particulate is titanium dioxide, tin oxide, zirconia, alumina, tantalum oxide, or a combination thereof. In an example, the ceramic particulate is titanium dioxide or tin oxide. In another example, the ceramic particulate is titanium dioxide. In a particular example, the ceramic particulate is a fumed ceramic particulate.

In an additional example of the first, second, and third aspects and the above examples, the solid buffer particulate has a specific surface area in the range of 50 $m^2/g$ to 350 $m^2/g$. For example, the specific surface area is in a range of 100 $m^2/g$ to 300 $m^2/g$, such as a range of 150 $m^2/g$ to 300 $m^2/g$, or a range of 225 $m^2/g$ to 275 $m^2/g$. In an further example of the first, second, and third aspects and the above examples, the solid buffer particulate has a specific surface area in the range of 25 $m^2/g$ to 125 $m^2/g$, such as in a range of 50 $m^2/g$ to 100 $m^2/g$.

In another example of the first, second, and third aspects and the above examples, the solid buffer particulate has a particle size in a range of 0.01 microns to 1200 microns. For example, the particle size is in a range of 0.05 microns to 500 microns, such as a range of 0.5 microns to 200 microns or a range of 5.0 microns to 100 microns.

In a further example of the first, second, and third aspects and the above examples, the surfactant includes a nonionic surfactant.

In an additional example of the first, second, and third aspects and the above examples, the suspension further includes a biocide.

In another example of the first, second, and third aspects and the above examples, the suspension further includes a magnesium salt.

In a further example of the first, second, and third aspects and the above examples, the suspension includes a potassium salt.

In an additional example of the first, second, and third aspects and the above examples, the method further includes applying the filtered solution to a reagent concentrate to form a reagent solution. For example, the reagent concentrate includes a nucleotide.

In another example of the first, second, and third aspects and the above examples, the sensor is a pH sensor. In another example of the first, second, and third aspects and the above examples, the sensor is a biosensor.

In a further example of the first, second, and third aspects and the above examples, the sensor is a semiconductor sequencing sensor.

In an additional example of the first, second, and third aspects and the above examples, the method further includes repeating mixing and titrating.

In another example of the first, second, and third aspects and the above examples, the method further includes applying the dispersion to a cartridge.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of performing pH-sensitive processes, the method comprising:
    drawing a suspension from a reservoir, the suspension including a surfactant and a solid buffer particulate and having a target pH, wherein the solid buffer particulate includes a ceramic particulate, wherein the ceramic particulate is titanium dioxide or tin oxide;
    filtering the solid buffer particulate from the suspension to form a filtered solution; and
    flowing the filtered solution over a sensor.

2. The method of claim 1, wherein the solid buffer particulate has a point of zero charge of at least 1.2 pH units and not greater than 10 pH units different than the target pH.

3. The method of claim 2, wherein the point of zero charge is at least 2.0 pH units different than the target pH.

4. The method of claim 1, wherein the target pH is in a range of 6 to 8.

5. The method of claim 4, wherein the target pH is in a range of 6.8 to 8.0.

6. The method of claim 1, wherein the ceramic particulate is titanium dioxide or tin oxide.

7. The method of claim 1, wherein the ceramic particulate is a fumed ceramic particulate.

8. The method of claim 1, wherein the solid buffer particulate has a specific surface area in the range of 50 $m^2/g$ to 350 $m^2/g$.

9. The method of claim 1, wherein the solid buffer particulate has a specific surface area in the range of 25 $m^2/g$ to 125 $m^2/g$.

10. The method of claim 1, wherein the solid buffer particulate has a particle size in a range of 0.01 microns to 1200 microns.

11. The method of claim 10, wherein the particle size is in a range of 0.05 microns to 500 microns.

12. The method of claim 1, wherein the surfactant includes a nonionic surfactant.

13. The method of claim 1, wherein the suspension further includes a biocide.

14. The method of claim 1, wherein the suspension further includes a magnesium salt or a potassium salt.

15. The method of claim 1, further comprising applying the filtered solution to a reagent concentrate to form a reagent solution.

16. The method of claim 15, wherein the reagent concentrate includes a nucleotide.

17. The method of claim 1, wherein the sensor is a biosensor.

18. The method of claim 1, wherein the sensor is a semiconductor sequencing sensor.

19. The method of claim 9, wherein the specific surface area is in a range of 50 $m^2/g$ to 100 $m^2/g$.

20. The method of claim 11, wherein the particle size is in a range of 5.0 microns to 100 microns.

* * * * *